United States Patent
Gu

(10) Patent No.: US 12,383,527 B2
(45) Date of Patent: Aug. 12, 2025

(54) METHODS FOR TREATING TRIPLE NEGATIVE BREAST CANCER USING SALVIANOLIC ACID B

(71) Applicant: HOWARD UNIVERSITY, Washington, DC (US)

(72) Inventor: Xinbin Gu, Washington, DC (US)

(73) Assignee: Howard University, Washington, DC (US)

( * ) Notice: Subject to any disclaimer, the term of this patent is extended or adjusted under 35 U.S.C. 154(b) by 0 days.

(21) Appl. No.: 18/439,896

(22) Filed: Feb. 13, 2024

(65) Prior Publication Data

US 2024/0180867 A1 Jun. 6, 2024

Related U.S. Application Data

(62) Division of application No. 17/046,577, filed as application No. PCT/US2019/027029 on Apr. 11, 2019.

(60) Provisional application No. 62/656,204, filed on Apr. 11, 2018.

(51) Int. Cl.
*A61K 31/343* (2006.01)
*A61K 31/704* (2006.01)
*A61P 35/00* (2006.01)

(52) U.S. Cl.
CPC .......... *A61K 31/343* (2013.01); *A61K 31/704* (2013.01); *A61P 35/00* (2018.01)

(58) Field of Classification Search
CPC ..... C07D 307/86; A61P 35/00; A61K 31/343; A61K 31/704
See application file for complete search history.

(56) References Cited

U.S. PATENT DOCUMENTS

2015/0250723 A1* 9/2015 Rozencweig ........ A61K 31/704
424/450
2016/0143976 A1 5/2016 Yan et al.

FOREIGN PATENT DOCUMENTS

CN 101664400 B 4/2012

OTHER PUBLICATIONS

CN101664400: published Apr. 2012; Machine translation provided.*
International Search Report issued Jul. 1, 2019 in International Application No. PCT/US2019/027029.
Sha et al., "Abstract 2128: Salvianolic acid B inhibits both ER-a +/- breast cancer cell growth in vivo and in vitro", Cellular and Molecular Biology, vol. 71, Issue 8 Supplement, Apr. 2011, Abstract (4 pages total).
Sha et al., "Antitumor properties of Salvianolic acid B against triple-negative and hormone receptor-positive breast cancer cells via ceramidemediated apoptosis", Oncotarget, 2018, vol. 9, No. 91, pp. 36331-36343 (13 pages total).
Written Opinion of the International Searching Authority issued Jul. 1, 2019 in International Application No. PCT/US2019/027029.

* cited by examiner

*Primary Examiner* — Pancham Bakshi
(74) *Attorney, Agent, or Firm* — Sughrue Mion, PLLC

(57) ABSTRACT

The present disclosure provides methods related to treating triple-negative breast cancer (TNBC) in a mammal by administering salvianolic acid B (or a salt or solvate thereof) to promote ceramide-mediated apoptosis. In one form, the ceramide-mediated apoptosis of TNBC cells occurs by decreasing the level of one or more of glucosylceramide synthase and GM3 synthase in the subject through the use of an effective amount of salvianolic acid B. In another aspect, salvianolic acid B or its pharmaceutically acceptable salt or solvate is used as a medicament or in the manufacture of a medicament for treating TNBC.

8 Claims, 8 Drawing Sheets

METHODS FOR TREATING TRIPLE NEGATIVE BREAST CANCER USING SALVIANOLIC ACID B

CROSS-REFERENCE TO RELATED APPLICATION

This application is a divisional of U.S. application Ser. No. 17/046,577, filed on Oct. 9, 2020, which is a § 371 of PCT/US2019/27029, filed Apr. 11, 2019, which claims the benefit of U.S. Provisional Application No. 62/656,204, filed on Apr. 11, 2018.

STATEMENT OF FEDERALLY SPONSORED RESEARCH

This invention was made in part with U.S. Government support under NIH P20 CA118770. The U.S. Government may have certain rights in this invention.

FIELD

This application relates to the treatment of cancer by administering salvianolic acid B, and in particular to the treatment of triple-negative breast cancer.

BACKGROUND

Breast cancer is the most common cancer in women and the second highest lethal form of cancer in the United States. Studies have shown that the incidence of breast cancer has been gradually decreasing in the last two decades; however, women in the United States have a one in eight chance of developing breast cancer in their lifetimes.

About one third of breast cancer is triple-negative breast cancer ("TNBC"), presenting the lack of expression of estrogen receptor α (ER-α), progesterone receptor, and human epidermal growth factor receptor-2 (HER2). Due to the poor response to anti-hormonal treatment and chemotherapeutics, TNBC is considered an aggressive form of breast cancer. The commonly used therapeutic agents for breast cancer, including doxorubicin, have little success in treating patients with TNBC. Doxorubicin also has limited clinical application due to the risk of cardiotoxicity.

A need exists for an effective treatment of triple-negative breast cancer without the significant side effects of doxorubicin.

SUMMARY

Salvianolic acid B (Sal-B) is a natural compound extracted from *Salvia miltiorrhiza* Bunge, a well-known Chinese herbal medicine for preventing and treating vascular diseases.

As described herein, Sal-B has surprisingly been found to have a high potency against triple negative breast cancer (TNBC), which is mediated at least in part by inhibiting tumor cell growth and enhancing ceramide-mediated apoptosis through GCS-catalyzed ceramide glycosylation.

In one aspect, a method of treating breast cancer in a subject in need thereof is provided. The method comprises administering a therapeutically effective amount of Sal-B to the subject. In one particular approach, the breast cancer is TNBC.

In accordance with one aspect of the present disclosure, a method for treating cancer in a subject includes inducing ceramide-mediated apoptosis of cancer cells by decreasing the level of one or more of glucosylceramide synthase and GM3 synthase in the subject through the use of an effective amount of Sal-B. In one particular approach, the cancer is TNBC.

A method of inducing ceramide-mediated apoptosis by decreasing the level of one or more of glucosylceramide synthase and GM3 synthase in cancer cells of a subject is also provided. The method comprises administering to said subject an effective amount of Sal-B.

Sal-B may be administered by any suitable route, including any of intravenous, oral, parenteral, intraperitoneal, intramuscular, intrathecal, subcutaneous, transdermal, vaginal, rectal, sublingual, buccal, nasal, topical, or inhalation spray. In one aspect, the Sal-B is administered once a day. In another aspect, the Sal-B may be administered at a dose of about 0.1 µg to about 500 mg/kg.

In any of the embodiments or aspects described herein, Sal-B may be provided in the form of a pharmaceutically acceptable salt or solvate. In one aspect, the pharmaceutically acceptable salt may be an aluminum salt, calcium salt, iron salt, magnesium salt, manganese salt, or combination thereof.

In yet another approach, the method further includes administering at least one additional therapy to the subject. For example, the at least one additional therapy may comprise one or more of radiotherapy, surgery, chemotherapeutic agent, hormone ablation therapy, pro-apoptosis therapy, and immunotherapy. In one aspect, the chemotherapeutic agent may comprise doxorubicin.

In yet another approach, Sal-B or a pharmaceutically acceptable salt or solvate thereof is provided for use in the manufacture of a medicament for treating triple negative breast cancer is provided. In another approach, Sal-B or a pharmaceutically acceptable salt or solvate thereof is provided for use as a medicament for treating triple negative breast cancer.

The medicament may be formulated for administration by at least one of intravenous, oral, parenteral, intraperitoneal, intramuscular, intrathecal, subcutaneous, transdermal, vaginal, rectal, sublingual, buccal, nasal, topical, or inhalation spray administration. In one aspect, the Sal-B is formulated at a dose of about 0.1 µg to about 500 mg/kg. In another aspect, the pharmaceutically acceptable salt is an aluminum salt, calcium salt, iron salt, magnesium salt, manganese salt, or a combination thereof.

In any of the aspects described herein, the subject may be a mammal, and preferably is a human.

DETAILED DESCRIPTION

Figure 1:
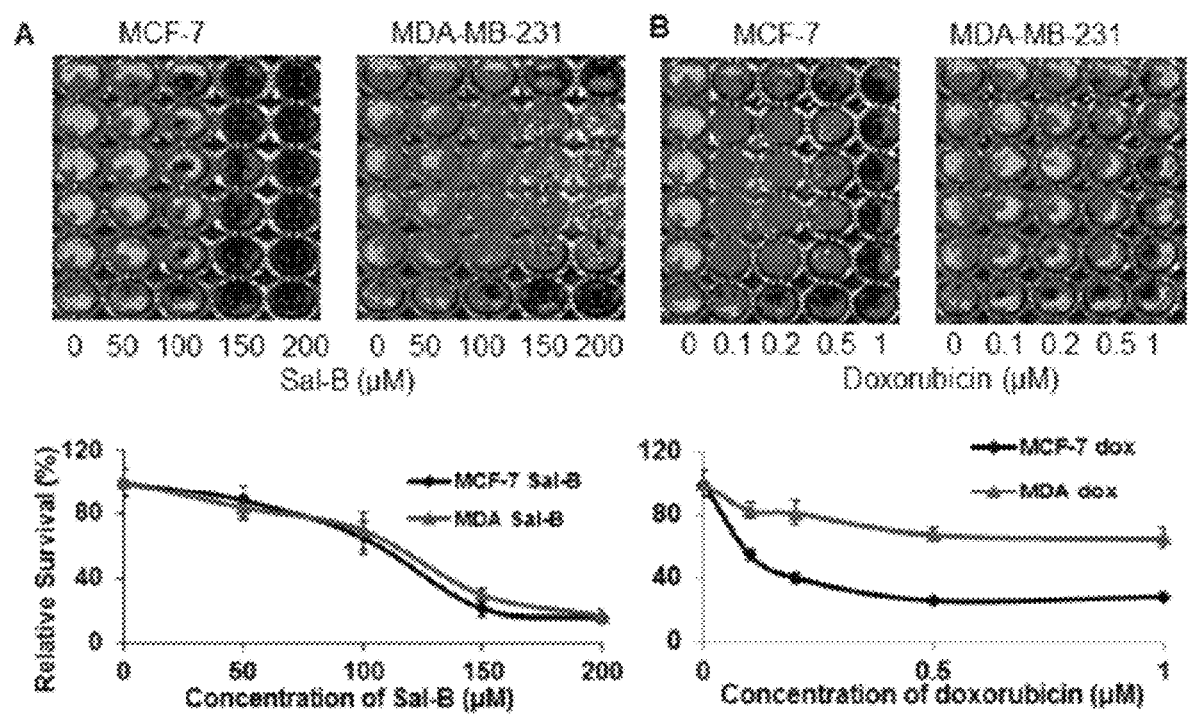
FIG. 1 includes luciferase-based bioluminescent images and graphs showing the relative survival percentage of MDA-MB-231 ("MDA") and MCF-7 cells after exposure to various concentrations of Sal-B and doxorubicin. Inhibitory effects of Sal-B on the cell viability and colony formation of both triple-negative MDA cells and hormone-receptor positive MCF-7 breast cancer cells are demonstrated. The cell viability was analyzed by luciferase-based bioluminescent imaging after exposure to Sal-B (50 µM, 100 µM, 150 µM and 200 µM) (panel A) and doxorubicin (0.1 µM, 0.2 µM, 0.5 µM and 1 µM) (panel B) for 24 hours, respectively. There were significant differences in the cell viability between untreated and Sal-B treated cells (P<0.05). No significant difference was observed for the effect of Sal-B on the cell viability between MDA cells and MCF-7 cells (P>0.05), different from that of doxorubicin (P<0.05).

Salvianolic acid B (Sal-B) is a natural compound extracted from *Salvia miltiorrhiza* Bunge, a well-known Chinese herbal medicine for preventing and treating vascular diseases. Sal-B has the following structure:

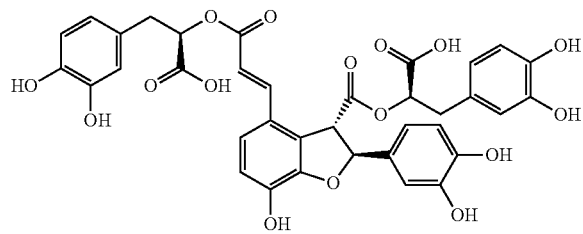 [SMILES: O=C(/C=C/c1ccc(O)c2c1[C@H](C(=O)O[C@H](Cc1ccc(O)c(O)c1)C(=O)O)[C@@H](c1ccc(O)c(O)c1)O2)O[C@H](Cc1ccc(O)c(O)c1)C(=O)O]

As described herein, Sal-B has surprisingly been found to have a high potency against triple-negative breast cancer (TNBC), which is mediated at least in part by inhibiting tumor cell growth and enhancing ceramide-mediated apoptosis through GCS-catalyzed ceramide glycosylation. TNBC is considered a very aggressive form of breast cancer and has been challenging to treat due to the poor response to anti-hormonal treatment and chemotherapeutics.

Described herein are methods of treating cancer in a subject in need thereof comprising administering Sal-B to the subject. In one aspect, the cancer may be treated by inducing ceramide-mediated apoptosis in cancer cells by administering a therapeutically effective amount of Sal-B. In another aspect, the cancer is treated by enhancing ceramide-mediated apoptosis by decreasing expression of glucosylceramide synthase and/or GM3 synthase. Significantly, early inhibition of GCS has potential to prevent drug resistance. The cancer being treated is one in which ceramide-mediated apoptosis can be induced via the decrease in expression of one or more of glucosylceramide and GM3 synthase. In one aspect, the cancer being treated is breast cancer, and in a more particular aspect, the cancer being treated is triple-negative breast cancer (TNBC).

While previous studies have found that Sal-B has a suppressing effect against head and neck squamous carcinoma cells via dose-dependent inhibition of prostaglandin $E_2$ synthesis and inhibition of COX-2 expression, it was surprisingly found herein that Sal-B was effective to increase ceramide accumulation and inhibit anti-apoptotic protein expression in TNBC cells. Interestingly, the ceramide accumulation was accompanied by decreased expression of glucosylceramide and GM3 synthases, which are two key enzymes regulating ceramide metabolism. By the present disclosure, it was demonstrated that Sal-B exerts its antitumor effects at least partially by inducing the ceramide accumulation and ceramide-mediated apoptosis via inhibiting the expression of glucosylceramide and GM3 synthases, which was independent of estrogen receptor $\alpha$.

As generally used herein, the term "subject" refers to a mammalian subject, in one particular aspect a human subject, in need of a treatment. In one particular aspect, the subject may be any one of a subject having been diagnosed with a cancer (such as TNBC), a subject undergoing treatment for any disorder including a cancer (such as TNBC), an asymptomatic subject having undergone a test or scan indicative of an underlying condition, a symptomatic subject having undergone a test or scan indicative of an underlying condition, a subject undergoing clinical treatment including cancer therapy or clinical intervention in the form of drugs, chemotherapy, immunotherapy, surgery, radiation or therapeutic devices, or not yet undergoing any clinical treatment.

As used herein, the terms "treatment," "treating," and the like refer to an intervention performed to alter the pathology of, or carrying out a procedure, to obtain a desired pharmacologic and/or physiologic effect. The effect may be therapeutic in terms of effecting a partial or complete cure for a disease, condition, symptom, and/or adverse effect attributable to the disease or condition. These terms also cover any treatment of a condition or disease in the subject, and include: (a) inhibiting the disease, i.e., arresting its development; (b) causing regression of the disease; (c) reducing the severity of a symptom of the disease; and/or (d) reducing the frequency of a symptom of the disease or condition.

The terms "cancer" and "cancerous" refer to or describe the physiological condition in mammals that is typically characterized in part by unregulated cell growth. As used herein, the term "cancer" refers to non-metastatic and metastatic cancers, including early stage and late stage cancers. As noted above, the cancer being treated herein is one in which ceramide-mediated apoptosis can be induced via the decrease in expression of at least one of glucosylceramide synthase and GM3 synthase. In one aspect, the cancer is breast cancer. In another particular aspect, the cancer is TNBC.

A therapeutically effective amount may be an amount sufficient to provide an observable therapeutic benefit. As used herein, the terms "therapeutically effective amount" or "effective amount" refer to the amount of Sal-B and/or other active ingredient required to confer a biological or meaningful benefit to the subject, such as a biological or medical response or improvement sought by a medical doctor or other medical professional. In one aspect, the terms "therapeutically effective amount" or "effective amount" are intended to mean the amount of Sal-B and/or other active ingredient that will bring about a biologically meaningful improvement in a subject's symptom or prognosis. Doses that exhibit large therapeutic indices are preferred. Effective amounts may vary, as recognized by those skilled in the art, depending, for example, on route of administration, dosage form, inclusion of additional active agents, as well as age, weight, sensitivity, and health of the subject.

In any of the embodiments described herein, the Sal-B may be in the form of a pharmaceutically acceptance salt or solvate. A pharmaceutically acceptable salt may be any salt which retains the activity of the parent compound and does not impart any unduly undesirable effects on a subject to whom it is administered and in the context in which it is administered. Pharmaceutically acceptable salts may include, but are not limited to, metal salts such as aluminum, calcium, iron, magnesium, manganese, and complex salts.

In another aspect of the present disclosure, a method is provided for inducing ceramide-mediated apoptosis by decreasing the level of one or more of glucosylceramide synthase and GM3 synthase in a subject diagnosed with TNBC. The method comprises administering an effective amount of Sal-B to the subject. In another aspect of the present disclosure, ceramide-mediated apoptosis may be induced by decreasing the level of GM3 synthase by administering an effective amount of Sal-B to the subject. The levels of GCS and GM3 synthases may be increased alone or in conjunction, at the same level or at different levels, and at the same rate or at different rates in accordance with the present disclosure.

Sal-B may be administered by any appropriate method, such as intravenous, oral, intraperitoneal, parenteral, intramuscular, intrathecal, subcutaneous, transdermal, vaginal, rectal, sublingual, buccal, nasal, topical, inhalation spray, or any combination thereof.

Sal-B can be prepared in a variety of forms and may comprise a variety of optional ingredients. For example, the formulation may include ingredients such as but not limited to preservatives, lubricant, stabilizer, colorant, diluent, isotonic agent, pH modifier, buffer, excipient, and the like and additional active ingredients, if desired. In some approaches, any additional ingredients included in the composition should not negatively impact the stability of the Sal-B and any other active ingredient(s) in the composition. For example, a liquid formulation can be prepared, such as, for example, in the form of a solution, emulsion, or suspension in a non-toxic, pharmaceutically-acceptable carrier. Exemplary pharmaceutically-acceptable carriers include saline, buffered saline, isotonic saline, Ringer's solution, dextrose, sterile water, deionized water, glycerol, ethanol, 5% dextrose in water, and combinations thereof. In another aspect, the drug may be a powder or lyophilisate that is reconstituted with a solvent prior to use. In yet another aspect, the formulation may be in the form of an emulsion or liquid concentrate that is suitable for dilution prior to administration. In one aspect, the form of composition is a sterile injectable, which may be aqueous or in a suspension. In some embodiments, excipients, surfactants, stabilizers, carriers, or a combination thereof may be employed for delivery of the medicament. In some embodiments, dosage forms may be immediate-release. In other embodiments, dosage forms may be sustained-release.

For oral administration, the Sal-B or its salt or solvate may be provided in a form including, but not limited to, capsules, tablets, pills, aqueous suspensions, or solutions. When aqueous suspensions are required for oral use, the active ingredient may be combined with emulsifying and suspending agents. Certain sweetening, flavoring, or coloring agents, or a combination thereof may also be added.

In some embodiments of the present disclosure, the method of treatment may include administering at least one additional therapy to the subject. The at least one additional therapy may comprise one or more of radiotherapy, surgery, therapeutic agent, hormone ablation therapy, pro-apoptosis therapy, and immunotherapy. The additional therapeutic agent may be, for example, chemotherapeutic, antimicrobial, antifungal, antiviral, anti-inflammatory, or a combination thereof. In some embodiments, the chemotherapeutic agents may be anthracyclines, such as doxorubicin, daunorubicin, and idarubicin; taxanes, such as docetaxel and paclitaxel; pyrimidine antagonists, such as cytarabine, 5-fluorouracil, gemcitabine, and capecitabine; or vinca alkaloids, such as vincristine and vinblastine.

In one approach, the at least one additional therapy may be administered concurrently with the administration of Sal-B. The term "concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about 24 hours before or after another. Any contemporaneous time may be useful. However, it will often be the case that when not administered simultaneously, the agents will be administered within about one minute to within about eight hours and suitably within less than about four hours, in another aspect less than about 1 hour. When administered contemporaneously, the agents are suitably administered at the same site on the subject. The term "same site" includes the exact location but can be within about 0.5 to about 15 centimeters, preferably from within about 0.5 to about 5 centimeters. The term "separately" as used herein means that the agents are administered at an interval, for example at an interval of about 24 hours to several weeks or months. The active agents may be administered in either order. The term "sequentially" as used herein means that the agents are administered in sequence, for example at an interval or intervals of minutes, hours, days, or weeks. If appropriate the active agents may be administered in a regular repeating cycle.

In one aspect of the present disclosure, Sal-B may be administered once a day (i.e., a 24-hour period). In other methods, Sal-B may be administered more than once a day. In yet other methods, Sal-B may be administered at least once per week but more infrequently than once a day.

The administered dose may be about 0.1 μg/kg (μg per kg bodyweight) to about 500 mg/kg, in another aspect about 0.1 μg/kg to about 100 mg/kg or about 100 μg/kg to about 1 mg/kg. For example, the dose may be about 10 μg/kg to about 20 μg/kg, about 20 μg/kg to about 30 μg/kg, about 30 μg/kg to about 40 μg/kg, about 40 μg/kg to about 50 μg/kg, about 50 μg/kg to about 60 μg/kg, about 60 μg/kg to about 70 μg/kg, about 70 μg/kg to about 80 μg/kg, about 80 μg/kg to about 90 μg/kg, about 90 μg/kg to about 100 μg/kg, about 100 μg/kg to about 200 μg/kg, about 200 μg/kg to about 300 μg/kg, about 300 μg/kg to about 400 μg/kg, about 400 μg/kg to about 500 μg/kg, about 500 μg/kg to about 1 mg/kg, about 1 mg/kg to about 100 mg/kg, and about 100 mg/kg to about 500 mg/kg. However, an optimal dosage may be determined empirically for each subject being treated and may depend upon a variety of factors, including the activity of the agents; the age, body weight, general health, and diet of the individual; the time and route of administration; and other medications the individual is taking. Optimal dosages may be established using routine testing and procedures that are well known in the art.

In yet another approach, Sal-B or a pharmaceutically acceptable salt or solvate thereof is provided for use in the manufacture of a medicament for treating triple negative breast cancer is provided. In another approach, Sal-B is provided for use as a medicament for treating triple negative breast cancer. The medicament may be formulated for administration by at least one of intravenous, oral, parenteral, intraperitoneal, intramuscular, intrathecal, subcutaneous, transdermal, vaginal, rectal, sublingual, buccal, nasal, topical, or inhalation spray administration. In one aspect, Sal-B is formulated at a dose of about 1 μg to about 100 mg/kg. In another aspect, the pharmaceutically acceptable salt is an aluminum salt, calcium salt, iron salt, magnesium salt, manganese salt, or a combination thereof.

Advantages and embodiments of the method and compositions described herein are further illustrated by the following example; however, the particular conditions, processing schemes, compositions, and amounts thereof recited in these examples, as well as other conditions and details, should not be construed to unduly limit this method. All percentages are by weight unless otherwise indicated.

EXAMPLE

To assess the effects of Sal-B on cell viability, cell cycle, and apoptosis in cultured triple negative breast cancer (TNBC) cells and tumor xenografts, the human triple negative MDA-MB-231 (hereinafter "MDA") breast cancer cell line (test group) and the human estrogen receptor α positive MCF-7 (hereinafter "MCF-7") breast cancer cell line (control group) were compared.

Cell lines and culture. MCF-7 and MDA human breast cancer cell lines stably transfected with firefly luciferase gene were purchased from Caliper Life Sciences (Hanover, MD). MCF-7 cells were cultured in DMEM medium (Invitrogen, Carlsbad, CA) and MDA cells were grown in DMEM/F-12 (1:1) medium (Invitrogen). Both media were supplemented with 10% fetal bovine serum (Invitrogen) and antibiotic-antimycotic mixture (100 IU/ml penicillin and 100 μg/ml streptomycin; Cellgro). The cells were maintained at 37° C. in 5% $CO_2$. All experiments were performed when the cells were in the logarithmic phase of growth.

Preparation of Sal-B and Doxorubicin. Doxorubicin was extracted from commercially available Adriamycin solution (Bedford Lab, Bedford, OH).

Sal-B was extracted from *Salvia miltiorrhiza* Bunge powder with 70% ethanol in a Soxhlet extractor. The extract was then passed through a D101 Macroporous resin and the magnesium salt of Sal-B was eluted with a six-fold column volume of about 20-40% ethanol solutions. The Sal-B magnesium salt-rich fraction in 40% ethanol was concentrated and converted into free Sal-B by adjusting to pH 3-4 with hydrochloric acid. The free Sal-B was dried and dissolved in water and purified with a polyamide chromatographic column. The highly purified Sal-B (>95%) was analyzed with high-pressure liquid chromatography. Before use, the purified Sal-B was dissolved in molecular grade water.

Statistical analysis. Values represent the means±SD of a minimum of three replicate tests. Data were analyzed by the Duncan test following the ANOVA procedure when multiple comparisons were made. Differences were considered significant when $P<0.05$.

Antibodies. The monoclonal or polyclonal antibodies against ceramides, survivin, Bcl-xL, caspase-3, caspase-8, cyclin A, cyclin B1, and PCNA were purchased from Sigma (St. Louis, MO). The anti-ceramide monoclonal antibody (clone: MID 15B4) recognizes free and bound ceramides and its reactivity is species independent. The antibodies against ß-actin and p-ERK were obtained from Santa Cruz (Santa Cruz, CA). The antibodies against GCS and GM3 synthase were obtained from NOVUS (Cambridge, UK) and anti-ER-α antibody was from Dako (Carpinteria, CA).

Luciferase assay. The MDA cell line and the hormone receptor-positive MCF-7 cell line were utilized to test the effectiveness of Sal-B and doxorubicin on cancer cell viability. Both cell lines had been stably transfected and expressed the firefly luciferase gene. The bioluminescent signal intensity reflects the cell metabolic activity, being highly correlated with the cell viability. Cell viability was evaluated using the sensitive bioluminescent optical imaging.

The cells (10,000 per well) were seeded in flat-bottomed 96-well plates in the above-identified medium with 10% fetal bovine serum and allowed to grow overnight. The old medium was then replaced with fresh medium containing different concentrations of Sal-B (50, 100, 150, and 200 μM) or doxorubicin (0.1, 0.2, 0.5, and 1 μM). The cells were further cultured for 24 hours and D-luciferin was added to each well and mixed gently (final concentration of 150 μ/ml). The signal was measured with the Xenogen IVIS 200 imaging system (Caliper Life Sciences, Hopkinton, MA, USA). The system was equipped with a highly sensitive, cooled charge-coupled device (CCD) camera and a light-tight specimen box. Imaging and quantification of signals was controlled by the acquisition and analysis software Living Image 3.0. The bioluminescent signal from the cells in each well was expressed as total flux (photons per second (p/s)). At least five replicates were performed in each experiment, and each experiment was repeated at least three times. The representative data are presented.

Referring to FIG. 1, similar inhibitory effects of Sal-B were observed on the cell viability of both MDA and MCF-7 cells in a dose-dependent manner. Compared with untreated cells, MDA and MCF-7 cells decreased their cell viabilities to 69% and 65%, respectively, when treated with Sal-B at 100 μM for 24 hours (FIG. 1, panel A). The half maximal inhibitory concentrations ($IC_{50}$) were 125 μM for MDA cells and 120 μM for MCF-7 cells (FIG. 1, panel C). No significant difference in the inhibitory effect of Sal-B between the two cell lines was observed. At 0.5 μM concentration, doxorubicin reduced the viability of MCF-7 cells by approximately 67%, whereas there was only 25% reduction for the MDA cells (P<0.05). No further reduction of the cell viability was observed in both cell lines treated with 1 μM doxorubicin. Accordingly, the results demonstrated that Sal-B was able to reduce the cell viability of both MDA and MCF-7 cells in vitro; showing an $IC_{50}$ of 125 μM for MDA cells and 120 μM for MCF-7 cells. The effect of doxorubicin (1 μM) on the cell viability was approximately two-fold higher for MCF-7 cells than for MDA cells.

Colony formation assay. The inhibitory effect of Sal-B was further confirmed by colony formation assay. The colony formation assay was performed as described previously (Hao Y, et al., "Enforced expression of miR-101 inhibits prostate cancer cell growth by modulating the COX-2 pathway in vivo," Cancer Prev Res (Phila). 2011; 4: 1073-1083). Briefly, MDA cells were seeded at a density of 300 cells per well in 6-well plates, cultured overnight, and then treated with Sal-B at different concentrations (1, 10, 20, 50, and 100 μM) for 24 hours. Following treatment, the old medium containing Sal-B was replaced with fresh drug-free media and the cells were allowed to grow for 10 days to permit colony formation from viable clonogenic cells. Colonies were stained with 0.1% trypan blue in 50% ethanol and were counted manually under microscopy with a grid printed on a transparent plastic sheet to keep track of colonies counted. The colonies containing more than 50 cells were considered to represent a viable clonogenic cell. The experiment was completed in triplicate for each treatment.

Figure 2:
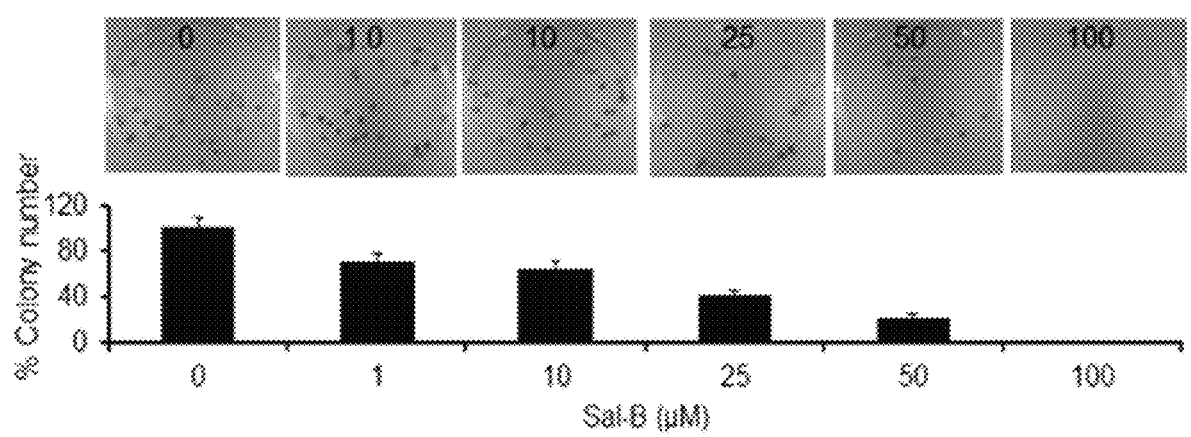
FIG. 2 includes photographs and bar graphs showing the colony formation ability of MDA and MCF-7 cells after exposure to various concentrations of Sal-B and doxorubicin. The colony formation of MDA cells was determined with colony formation assay after exposure to various doses of Sal-B (1 μM, 10 μM, 25 μM, 50 μM and 100 μM) for 24 h and colonies were allowed to grow for 10 days. A colony containing more than 50 cells was considered to represent a viable clonogenic cell. The results represent the mean±SD. There were significant differences for the colony formation capability between untreated and Sal-B treated cells (P<0.05).

There were significant differences in the cell viability and colony formation capability between untreated and Sal-B treated cells (P<0.05). As shown in FIG. 2, the colony formation capability of the cells treated at the concentration of 1 μM was approximately 69% of that of the control cells, and a complete inhibition of the cell colony formation capability was observed at 100 μM. The results represent the mean±SD (FIG. 2). These results indicate that Sal-B has an inhibitory effect on TNBC cell growth in vitro.

Cell cycle profile analysis using flow cytometry and Western blot analysis. To understand the effects of Sal-B on the cell cycle of cancer cells, the cell cycle profile was analyzed using flow cytometry. The cells from both cell lines were treated with Sal-B (50 and 100 M) or doxorubicin (0.1 and 1 μM) for 24 hours and then fixed in chilled 80% ethanol. The fixed cells were incubated in a solution containing 100 μg/mL RNase at 37° C. water bath for 45 minutes. Propidium iodide (final concentration of 50 μg/ml) was then added to the cells and incubated in a 37° C. water bath for another 15 minutes. The analysis was carried out with a FACStar flow cytometer (Becton Dickinson, San Jose, CA). Ten thousand cells per sample were analyzed, each sample was done in triplicate and the experiment was repeated three times.

Figure 3:
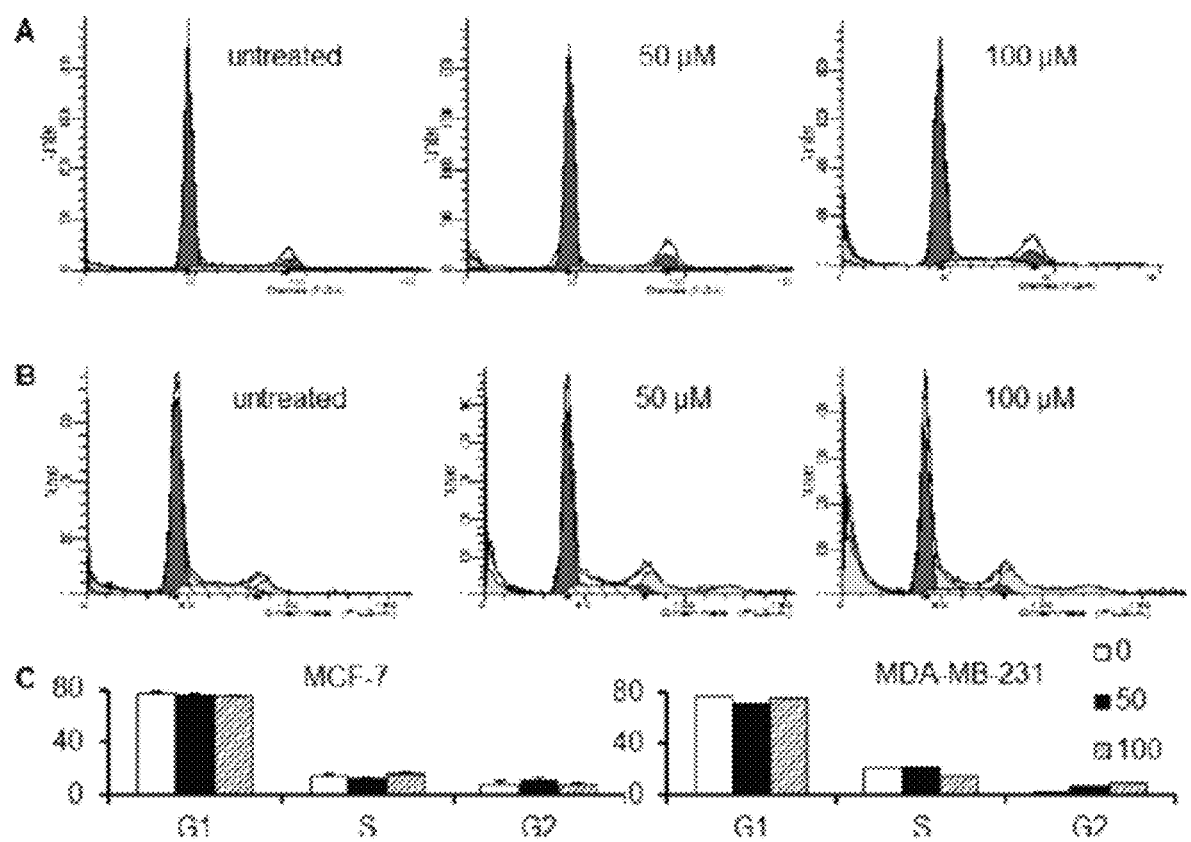
FIG. 3 includes flow cytometry plots and bar graphs showing the effects of Sal-B on cell cycle and cell cycle related protein expression in MCF-7 and MDA cells. Panels A and B show the DNA content profiles of MCF-7 and MDA cells, respectively, by flow cytometry. The percentages of cells in the different phases of cell cycle are summarized as mean±SD (panel C). No significant change was observed in the cell cycle phases of either MDA or MCF-7 cells after Sal-B treatment.

There were no significant changes in the cell cycle phases for either MDA or MCF-7 cells after exposure for 24 hours to Sal-B at concentrations of 50 μM (FIG. 3, panel A and FIG. 3, panel C) and 100 μM (FIG. 3, panel B and FIG. 3, panel C).

Figure 4:
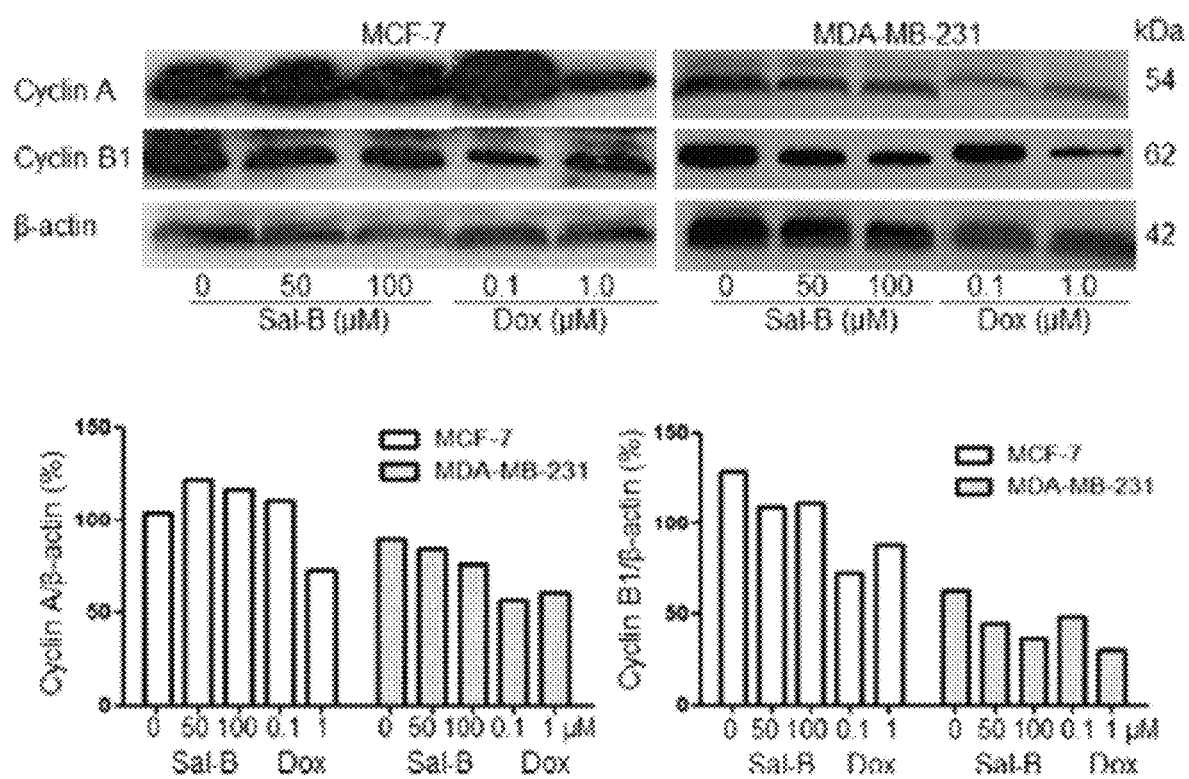
FIG. 4 includes Western blot results for the expression of cell cycle related protein cyclin A and cyclin B1. The expression of cyclin A and cyclin B1 was normalized by the expression of the internal control β-actin. The cells were treated with 50 μM and 100 μM Sal-B, respectively, for 24 hours. Doxorubicin (0.1 μM and 1 μM) was used as a control. For the cyclin A and cyclin B1 expression, downregulation of cyclin B1 but not cyclin A expression was found in both Sal-B treated MDA and MCF-7 cells. Treatment with 1 μM doxorubicin resulted in reduction of both cyclin A and cyclin B1 expression in both cell lines.

The expression of two cell cycle-related proteins—cyclin A and cyclin B1—was checked by Western blot. The expression of cyclin A and cyclin B1 was normalized by the expression of the internal control β-actin (lower panel). The cells were treated with 50 μM and 100 μM Sal-B, respectively, for 24 hours. Doxorubicin (0.1 μM and 1 μM) was used as a control. As shown in FIG. 4, down-regulation of cyclin B1 but not cyclin A expression was found in both Sal-B treated MDA and MCF-7 cells. Treatment with 1 μM doxorubicin resulted in reduction of both cyclin A and cyclin B1 expression in both cell lines. The results may be explained by that the cell cycle progression is controlled by a large set of molecules, although cyclin B1 is a key component in the control of cell cycle progression from G2 to M phase. Differently, doxorubicin effectively decreased the expression of both cyclin A and cyclin B1 in both cell lines.

Human tumor xenografts in athymic nude mice. The above findings showed that Sal-B could inhibit the proliferation of MDA cells in vitro, so the effects of Sal-B on the growth of MDA tumor xenografts in animals was then tested. The animal protocol was approved by the Howard University Animal Care and Use Committee. Four-week-old female athymic nude mice (Nu/Nu) were obtained from Harlan Sprague Dawley (Indianapolis, IN). All mice were provided the Harlan Teklad #2018 Global 18% protein rodent diet and water ad libitum. Mice were housed in temperature-controlled rooms (74±2° F.) with a 12-hour alternating light-dark cycle. MDA cells ($3 \times 10^6$/50 μL/spot) were subcutaneously injected into the both sides of lower back of mice using a 27-gauge needle. On day 10 after cell implantation, the mice with tumors (~5 mm in diameter)

were randomly divided into Sal-B treated, doxorubicin treated, and untreated groups (five mice per group), and were administrated Sal-B (80 mg/kg, three times per week), doxorubicin (4 mg/kg, every four weeks) and 0.9% saline (50 µl, three times per week), respectively, by intraperitoneal injection for a total of 37 days. (Our previous studies have shown that treatment with Sal-B at 80 mg/kg three times per week leads to no obvious side effects, but a higher dosage has resulted in the weight loss in some mice.) Mouse weight was measured once a week and tumor size was monitored by manual measurement with a caliper. All mice were sacrificed on day 37.

Figure 5:
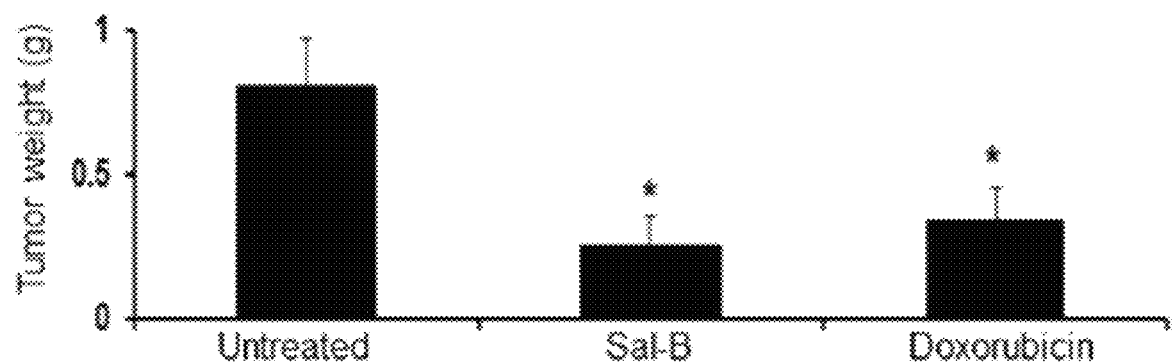
FIG. 5 is a bar graph showing the inhibitory effects of Sal-B on the growth of triple-negative MDA tumor xenografts in nude mice. The mice were treated with either Sal-B (80 mg/kg three times per week) or doxorubicin (4 mg/kg every 4 weeks) and all mice were sacrificed on day 37. The bar graph shows the tumor weights on day 37. The results represent the mean±SD and *P<0.05 means significant difference with respect to control mice.

As shown in FIG. 5, the average tumor weights of Sal-B treated group (0.26±0.06 g) and doxorubicin treated group (0.34±0.09 g) were both significantly smaller than that of untreated control group (0.81±0.12 g) (both $P<0.05$). During the experimental period, the body weights of mice were measured every week and there were no significant differences between untreated mice and treated mice (data not shown).

Immunohistochemical Staining and Western Blot Analysis

Immunohistochemical staining was performed as described previously (Hao Y, et al., "Enforced expression of miR-101 inhibits prostate cancer cell growth by modulating the COX-2 pathway in vivo," Cancer Prev Res (Phila), 2011; 4: 1073-1083). Deparaffinized specimens were first labeled with anti-PCNA, Bcl-xL, survivin, or ceramide antibody and secondary antibody sequentially. The slides were then stained with streptavidin-horseradish peroxidase and imaged with a microscope equipped with a camera and linked to a computer. For the quantification, ten high-magnification (40×) fields were randomly selected from each slide of tumors and the positive cells were counted. The protein expression was expressed as the average number of positive cells per high magnification field.

Figure 6:
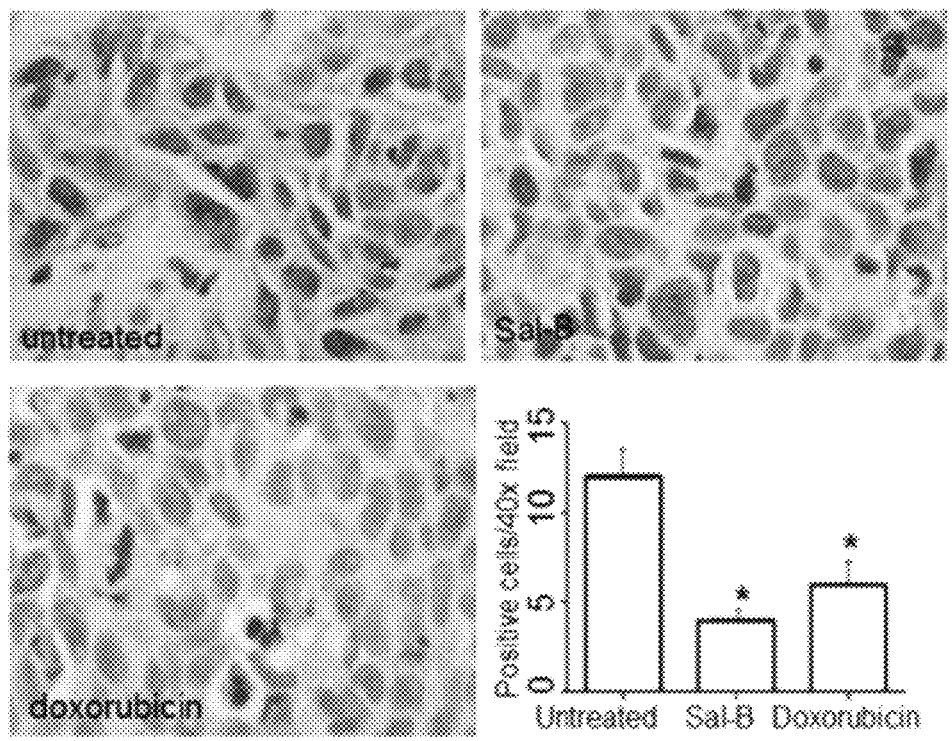
FIG. 6 includes immunohistochemical analysis for proliferating cell nuclear antigen (PCNA) levels in Sal-B treated and doxorubicin treated tumors. The PCNA levels were higher in untreated tumors than in Sal-B treated and doxorubicin treated tumors.

In parallel with the decreased tumor growth described above, the immunohistochemical analysis demonstrated that proliferating cell nuclear antigen (PCNA) levels were higher in untreated MDA tumor xenografts than in Sal-B treated and doxorubicin treated tumor xenografts (FIG. 6). The results represent the mean±SD and *$P<0.05$ means significant difference with respect to control mice.

Figure 7:
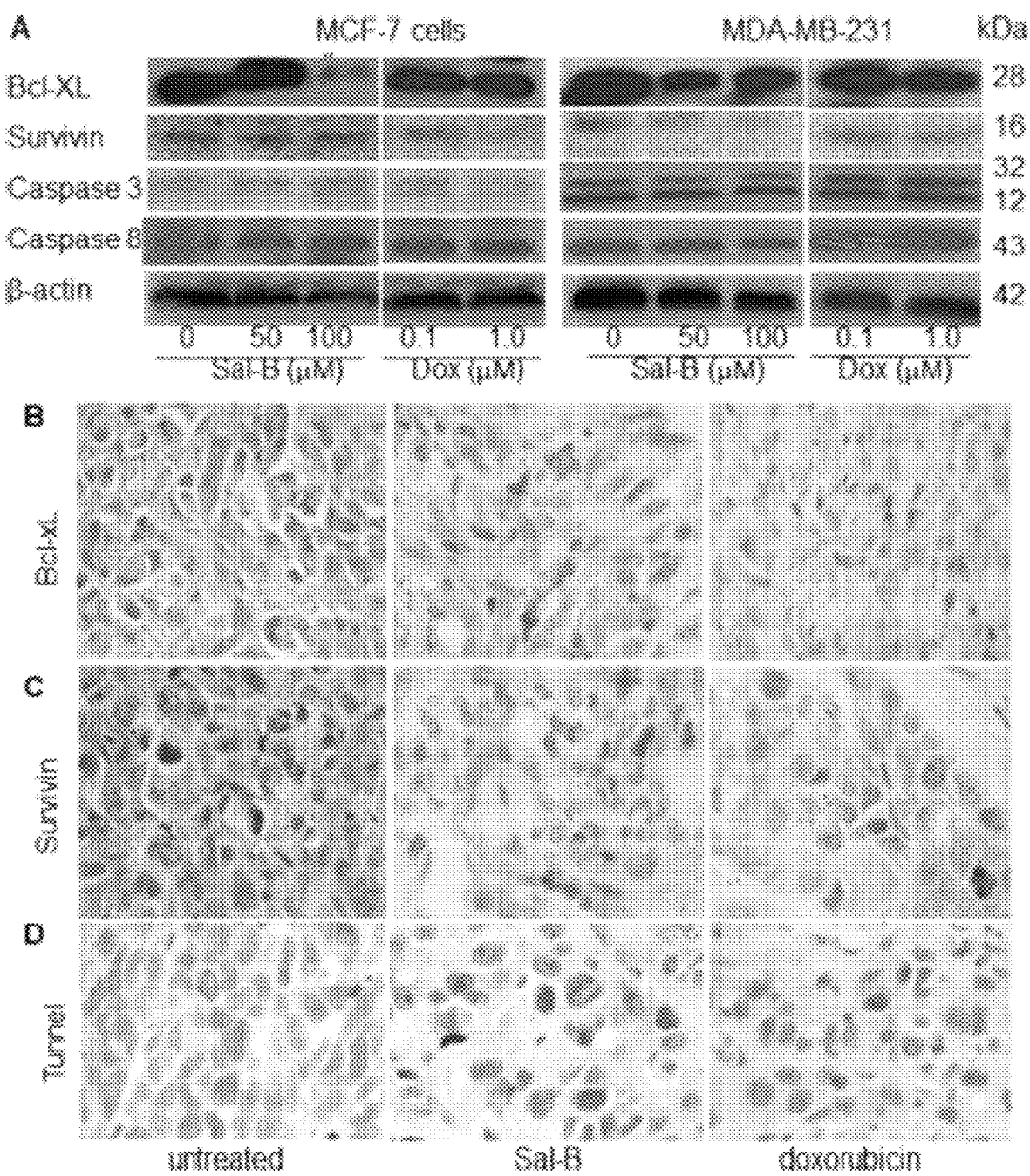
FIG. 7 includes Western blot and immunohistochemical analysis demonstrating the effects of Sal-B on the apoptosis in both MCF-7 and MDA cancer cells and tumor xenografts. As shown in panel A, Western blot analysis was used to determine the expression of apoptosis-related proteins Bcl-XL, survivin, caspase-3 and caspase-8. β-actin was used as an internal control. The cells were treated with Sal-B (50 μM and 100 μM) and doxorubicin (0.1 μM and 1 μM), respectively, for 24 hours. Both Sal-B and doxorubicin downregulated both Bcl-xL and survivin protein expression, but not the protein levels of caspase-3 and caspase-8 in the MDA and MCF-7 cell lines. Immunohistochemical analysis was used to detect the expressions of Bcl-xL (panel B) and survivin (panel C) in MDA tumor xenografts, showing decreased expression of Bcl-xL and survivin in the Sal-B and doxorubicin treated tumors than in the untreated tumors (P<0.05). Apoptotic cells in MDA tumor xenografts were analyzed by a TUNEL assay, showing an increase in apoptotic cells in the Sal-B and doxorubicin treated xenografts than in the untreated tumors (P<0.05) (panel D).

The expression of Bcl-XL decreased significantly in the Sal-B treated tumors (1.3±0.4) than in untreated tumors (11.8±3.0) ($P<0.05$) (FIG. 7, panel B). Survivin level showed similar changes, decreasing in Sal-B and doxorubicin treated groups compared to that in untreated group (FIG. 7, panel C).

Apoptotic cells in MDA tumor xenografts were also analyzed by a terminal deoxynucleotidyl transferase-mediated dUTP nick end labeling (TUNEL) assay using the TdT-FragEL DNA Fragmentation Detection Kit (EMD Millipore, Burlington, MA) as previously described (Li H, et al., "Cellular uptake and anticancer activity of salvianolic acid B phospholipid complex loaded nanoparticles in head and neck cancer and precancer cells," Colloids Surf B Biointerfaces. 2016; 147: 65-72). Briefly, sections were digested with proteinase K, and endogenous peroxidase activity was blocked with 3% hydrogen peroxide in 10 mM Tris (pH 8.0). The sections were then placed in equilibration buffer and incubated with TdT enzyme in a humid chamber at 37° C. for 1.5 hours. The apoptotic nuclei were stained by 3,3'-diaminobenzidine and observed by microscopy. The number of positively stained nuclei were manually counted and the percentage of positive cells versus the total number of cells was calculated. the highest number of apoptotic cells was found in the Sal-B treated xenografts (12.2±3.2), followed by doxorubicin treated xenografts (9.0±2.1), significantly different from that in the untreated tumors (3.1±1.8) (both $P<0.05$) (FIG. 7, panel D).

The immunohistochemical results were consistent with those from Western blotting (FIG. 7, panel A). Western blot analysis was used to determine the expression of apoptosis-related proteins Bcl-XL, survivin, caspase-3 and caspase-8 (FIG. 7, panel A). β-actin was used as an internal control for Western blotting. The MCD-7 and MDA cells were treated with Sal-B (50 µM and 100 µM) and doxorubicin (0.1 µM and 1 µM), respectively, for 24 hours. Proteins were extracted from the cells with RIPA lysis buffer (Santa Cruz Biotechnology, Santa Cruz, CA) and the protein concentrations were quantified with Bio-Rad protein quantification kit. Whole-cell proteins were separated on 8% SDS-polyacrylamide gel, transferred to the polyvinylidene difluoride membrane (Bio-Rad), and then probed with the indicated primary antibodies overnight at 4° C. Washed blots were then incubated with horseradish peroxidase-conjugated anti-rabbit, anti-mouse, or anti-goat antibody (Santa Cruz Biotechnology), respectively, for one hour at room temperature. Blots were developed and visualized with ECL detection system (Bio-Rad).

As shown in FIG. 7, panel A, both Sal-B and doxorubicin downregulated both Bcl-xL and survivin protein expression but not the protein levels of caspase-3 and caspase-8 in the MDA and MCF-7 cell lines.

Ceramide Levels

Sphingolipids, such as ceramides, play an important biological role in the regulation of proliferation, differentiation, and apoptosis of cancer cells. Intracellular ceramide accumulation has been shown to enhance the apoptosis of cancer cells. Development of drug resistance of cancer cells is also associated with an increase in ceramide glycosylation. Glucosylceramide synthase (GCS) is a key enzyme in converting ceramide to glucosylceramide, catalyzing the first reaction of ceramide glycosylation in sphingolipid metabolism. GM3 synthase catalyzes the initial step in the biosynthesis of most complex gangliosides from lactosylceramide. Both synthases closely regulate the ceramide metabolism. Early inhibition of GCS has the potential to prevent drug resistance.

Figure 8:
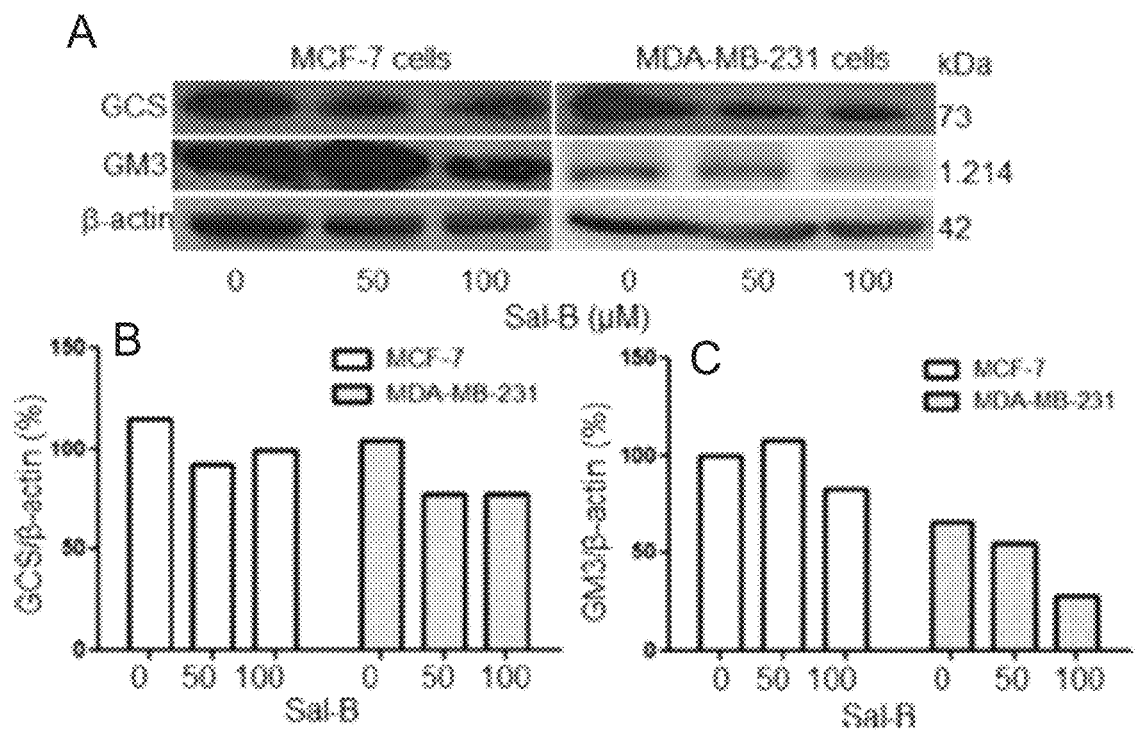
FIG. 8 includes Western blot results and bar graphs showing the expression of glucosylceramide synthase (GCS) and GM3 synthase in MDA and MCF-7 cells treated by various concentrations of Sal-B (panel A). The amount of protein expression was normalized by the expression of the internal control β-actin (panels B and C). Results demonstrated that Sal-B enhances ceramide accumulation and decreases the expression of GCS and GM3 enzymes.

To understand the mechanism underlying increased ceramide accumulation, the expression levels of GCS and GM3 synthase were measured by Western blot analysis in MDA and MCF-7 cells treated by various concentrations of Sal-B (FIG. 8). The amount of protein expression was normalized by the expression of the internal control β-actin. As shown in FIG. 8, a low dose (50 µM) of Sal-B was sufficient to inhibit GCS protein level in both MCF-7 and MDA cells. No further inhibitory effect was observed on GCS expression when treated with a higher dose (100 µM). The expression of GM3 synthase was also significantly diminished in the Sal-B-treated MDA cells at both 50 µM and 100 µM, and in the MCF-7 cells at 100 µM. Sal-B was found effective to down-regulate GCS and GM3 synthase expression in cancer cells.

Suppression of GCS and GM3 enzymes by Sal-B may lead to the accumulation of ceramides in cancer cells. As reported by others, doxorubicin has also been shown to induce ceramide accumulation in cancer cells by other studies. Both Sal-B and doxorubicin may induce TNBC cell apoptosis through the ceramide-mediated pathway. Early inhibition of GCS has potential to prevent drug resistance.

Ceramide levels were further analyzed with flow cytometry, according to the method described above, through comparison of Sal-B treated and untreated MDA cells. MDA cells were treated with 50 μM and 100 μM of Sal-B, respectively, for 24 hours and ceramide levels were then analyzed by flow cytometry. It was found that 50 μM of Sal-B was sufficient to enhance the ceramide level (FIG. 9, panel A).

Figure 9:
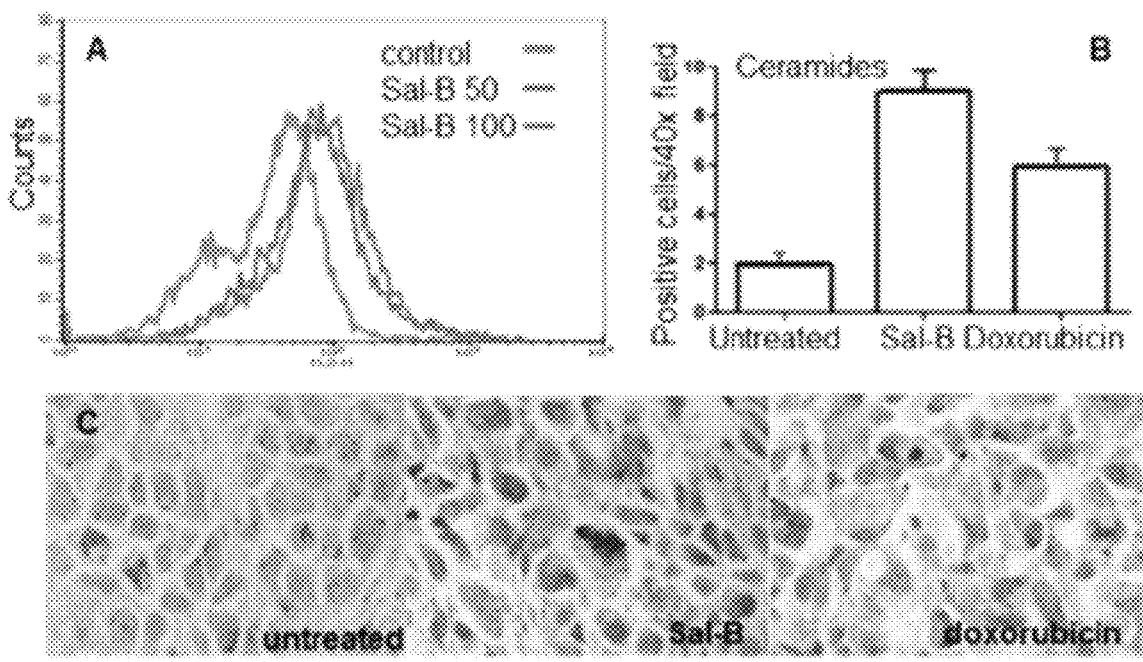
FIG. 9 includes a flow cytometry plot (panel A), bar graph (panel B), and immunohistochemistry images (panel C). MDA cells were treated with 50 μM and 100 μM of Sal-B, respectively, for 24 h and ceramide levels were then analyzed by flow cytometry (A). Immunohistochemistry was used to evaluate the expression of ceramides in MDA tumor xenografts (C) and the ceramide positive cells were counted (B).

Similarly, immunohistochemistry was carried out, as generally described above, to evaluate the expression of ceramides in MDA tumor xenografts (FIG. 9, panel C). The fixed cells were sequentially incubated with anti-ceramide primary antibody (1:100) for 2 hours and PE-labeled secondary antibody (1:200) for 30 minutes, and the ceramide positive cells were counted (FIG. 9, panel B). Ceramide levels significantly increased in both Sal-B-treated (9.6±2.4) and doxorubicin-treated (6.2±1.3) MDA tumor xenografts, compared to that in untreated control (2.3±0.7) (both $P<0.05$) (FIG. 9, panel B).

ER-α and p-ERK Expression

As noted above, triple-negative breast cancer presents the lack of expression of estrogen receptor α (ER-α), progesterone receptor, and human epidermal growth factor receptor-2 (HER2). To understand whether Sal-B regulated the expression of ER-α, the ER-α expression in MCF-7 cells was analyzed.

Figure 10:
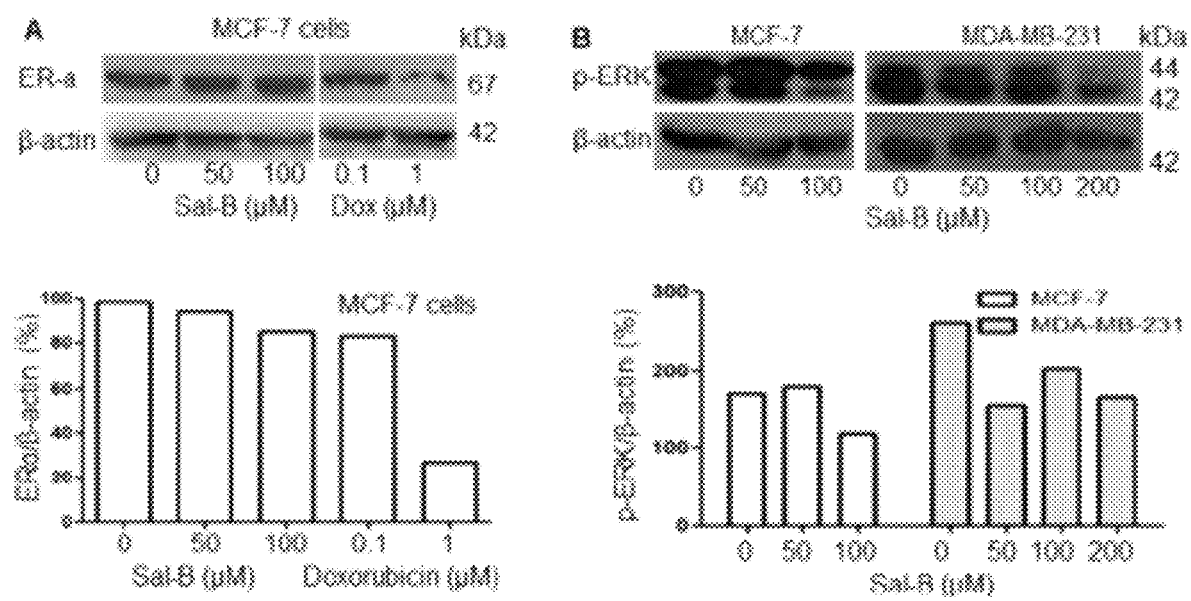
FIG. 10 includes Western blot images and bar graphs showing the effects of Sal-B on the ER-α and p-ERK expression in cancer cells. Panel A shows the ER-α expression in MCF-7 cells treated with Sal-B and doxorubicin and panel B shows the expression of p-ERK in MCF-7 and MDA cells following exposure to different concentrations of Sal-B for 24 hours. The amount of protein was normalized by that of the internal control β-actin.

FIG. 10, panel A shows the ER-α expression in MCF-7 cells treated with Sal-B and doxorubicin. The amount of protein was normalized by that of the internal control β-actin. The results showed that ER-α protein level was decreased by exposure to doxorubicin at the high dose (1 μM) but not to Sal-B (FIG. 10, panel A).

The MAPK/ERK pathway is a chain of proteins in the cells, which communicates a signal from a receptor on the surface of cells to the DNA in the nucleus of the cells, critical for establishing solid tumor growth, especially for breast cancer. P-ERK is a critical member in MAPK signal pathway and also a marker of the activation of MAPK signal pathway in up-regulating cell proliferation. Sal-B significantly decreased the p-ERK expression in both cell lines, suggesting that Sal-B might inhibit cell proliferation of TNBC cells by regulating MAPK signal pathway. Ceramides may interact with the MAPK pathway through inhibiting the p-ERK expression.

Because phospho-p44/42 extracellular signal-regulated kinases (p-ERK) is a key enzyme in the MAPK signal pathway, the expression of p-ERK was also investigated in MCF-7 and MDA cells following exposure to different concentrations of Sal-B for 24 hours. As shown in FIG. 10, panel B, p-ERK was down-regulated by Sal-B in both MCF-7 and MDA cells (FIG. 10, panel B).

While this disclosure has been particularly described with specific reference to particular processes and embodiments, it will be appreciated that various alterations, modifications, and adaptations may be based on the present disclosure, and are intended to be within the spirit and scope of the disclosure as defined by the following claims.

What is claimed is:

1. A method of treating triple-negative breast cancer in a subject in need thereof, the method comprising administering a therapeutically effective amount of salvianolic acid B or a pharmaceutically acceptable salt or solvate thereof to the subject,
wherein the subject is a human.

2. The method of claim 1, wherein the administering is by at least one of intravenous, oral, parenteral, intraperitoneal, intramuscular, intrathecal, subcutaneous, transdermal, vaginal, rectal, sublingual, buccal, nasal, topical, or inhalation spray administration.

3. The method of claim 1, wherein the salvianolic acid B is administered once a day.

4. The method of claim 1, wherein the salvianolic acid B is administered at a dose of about 0.1 μg to about 500 mg/kg.

5. The method of claim 1, wherein the pharmaceutically acceptable salt is an aluminum salt, calcium salt, iron salt, magnesium salt, manganese salt, or combination thereof.

6. The method of claim 1, further comprising administering at least one additional therapy to the subject.

7. The method of claim 6, wherein the at least one additional therapy comprises one or more of radiotherapy, surgery, chemotherapeutic agent, hormone ablation therapy, pro-apoptosis therapy, and immunotherapy.

8. The method of claim 7, wherein the chemotherapeutic agent comprises doxorubicin.

* * * * *